United States Patent [19]

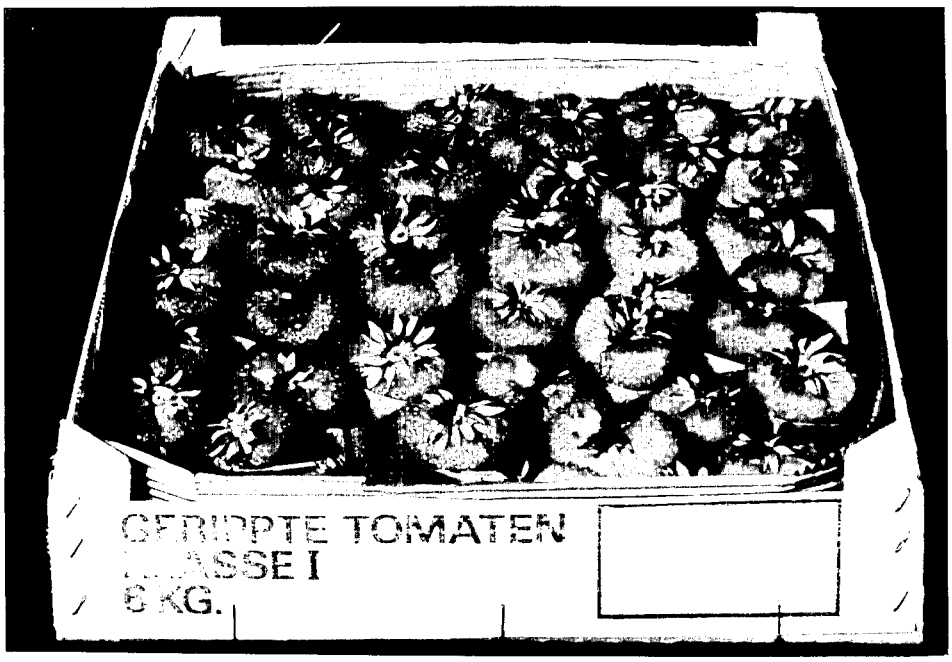
GERIPPTE TOMATEN
KLASSE I
6 KG.

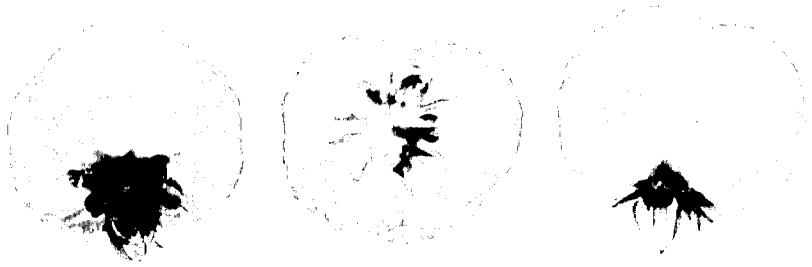
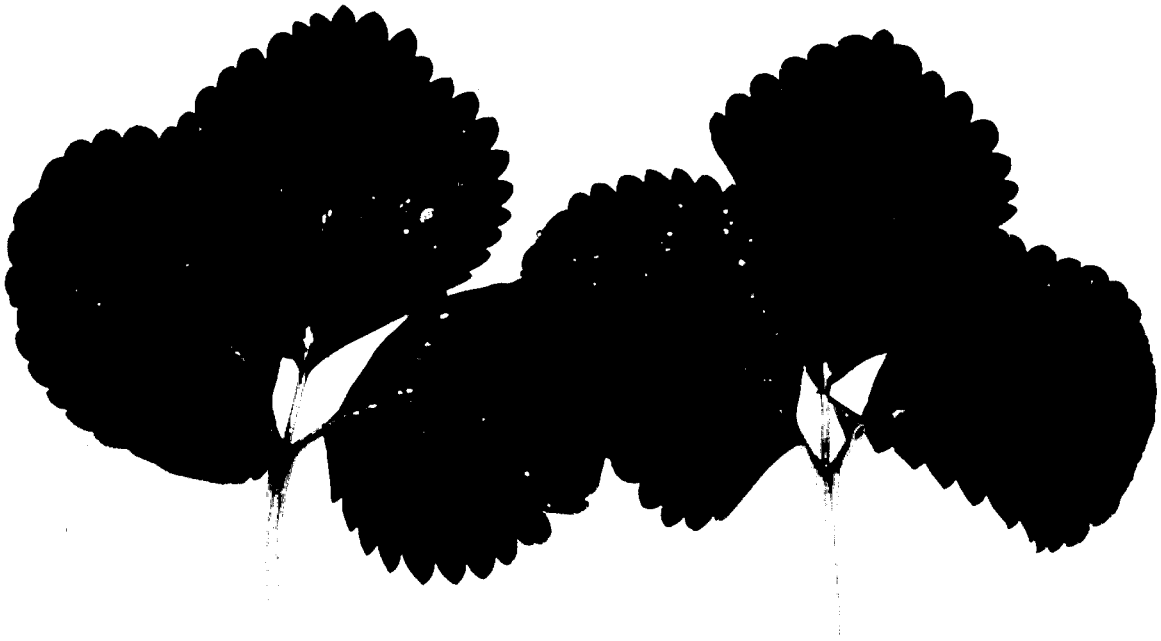

Somers

[11] Patent Number: Plant 5,782

[45] Date of Patent: Aug. 19, 1986

[54] STRAWBERRY PLANT NAMED MAXIM

[75] Inventor: Johannes A. Somers, AB Bergen op Zoom, Netherlands

[73] Assignee: Stichting Tuinbouw Proef-en Selectiebedrijf, Netherlands

[21] Appl. No.: 539,655

[22] Filed: Oct. 6, 1983

[51] Int. Cl.[4] ..... A01H 5/03

[52] U.S. Cl. ..... Plt./48

[58] Field of Search ..... Plt./48

[56] References Cited

U.S. PATENT DOCUMENTS

P.P. 5,232 5/1984 Cook ..... Plt./48

*Primary Examiner*—Robert E. Bagwill

*Attorney, Agent, or Firm*—Schwartz, Jeffery, Schwaab, Mack, Blumenthal & Evans

[57] ABSTRACT

A new and distinct variety of strawberry plant named Maxim characterized by its generally round and very large fruit.

2 Drawing Figures

1

The present invention relates to a new and distinctive variety of strawberry plant referred to by the varietal name Maxim.

The new cultivar is a product of a planned breeding program. The basic objective of the breeding program was to create a new variety of strawberry plant particularly characterized by its large fruit.

The new variety was originated from a cross made in a controlled breeding program in Middelrode, Netherlands. The female parent was a variety designated Gorella and the male parent was a variety designated Hummi Grande.

Maxim was discovered and selected by me as a plant within the progeny of the stated cross in a controlled environment comprising an experimental farm at Breda, Netherlands. Asexual reproduction of the new variety, as performed by me at Breda, Netherlands, has demonstrated that the combination of characteristics as herein disclosed for the new variety are firmly fixed and are retained through successive generations of asexual reproduction.

Maxim has not been observed under all possible environmental conditions. The phenotype may vary significantly with variations in environment. The following observations, measurements and values describe the new cultivar as grown in Breda, Netherlands, under conditions which closely approximate those generally used in commercial practice.

The following traits have been repeatedly observed and are determined to be basic characteristics of Maxim, which in combination distinguish this strawberry plant as a new and distinct variety:

1. Plant habit is similar to the paternal parent Hummi Grande.
2. Large, light green leaves.
3. Very large, but relatively few flowers.
4. Very large fruit, up to 7 cm. in diameter and 40–50 grams in weight.
5. Normal harvesting period.
6. Normal yield, 20,000 kilograms per hectare.

The new variety is similar to Hummi Grande in its leaf characteristics, but is distinguished therefrom by its much larger fruit.

The accompanying photographic drawings show fruit and leaves from a typical specimen plant of the new variety. FIG. 1 comprises fruit grown outdoors and shown packed in a container. FIG. 2 shows typical

2 leaves and fruit (in three different views) from a plant grown in a greenhouse, which accounts for the reduced fruit size relative to fruit grown outdoors as shown in FIG. 1. The colors appearing in the photographs are as true as possible with color illustrations of this type.

Parentage:

*Male parent.*—*Hummi grande.*

*Female parent.*—Gorella.

Propagation: Runner production is equal to other varieties currently being propagated in Netherlands, normal rooting and normal number of young plants.

Plants:

A. *Overall size.*—25–30 cm in height and in width.

B. *Preferred planting in Netherlands.*—Is August 1–10, with peak production occurring between June 15 and July 15.

C. *Leaves.*—1. Size: 8 cm or larger. 2. Shape: Generally round to heart shape, edges serrated. 3. Color: Dark green. 4. Growth habit: Vigorous.

Inflorescence:

A. *Formed.*—On long stems.

B. *Peduncles.*—5 or 6.

C. *Taste.*—Normal, not too sweet.

D. *Color-exterior and flesh.*—Outside and inside light red, exterior 45A-B (Royal Horticultural Society Chart) when ripe.

E. *Exterior surface.*—A little rough, non-glossy, firm.

F. *Characteristics of flesh and core.*—Average firmness.

G. *Keeping qualities.*—Good; the fruit retains its appearance and firmness during the normal shipping and marketing period.

H. *Flower size.*—Large, approximately 24 mm.

I. *Fruit size.*—Very large, 7 cm. and even greater in diameter, and weighing 40–50 grams.

Disease resistance: No special sensitivity to disease noted to date.

I claim:

1. A new and distinct variety of strawberry plant named Maxim, as described and illustrated, and particularly characterized by its generally round and very large fruit.

* * * * *